United States Patent
Nelson et al.

(10) Patent No.: US 8,663,562 B2
(45) Date of Patent: Mar. 4, 2014

(54) FLOW CELL FOR MEASURING ELECTROMAGNETIC RADIATION ABSORPTION SPECTRA IN A CONTINUOUSLY FLOWING IMMISCIBLE LIQUID(S) OR LIQUIDS WITH ENTRAINED GAS PHASES

(75) Inventors: Mark Erik Nelson, Mount Vernon, IN (US); Arkady Samuilovich Dykman, St. Petersburg (RU); Andrey Vladimirovich Zinenkov, St. Petersburg (RU); Alexey Leonidovich Moskvin, St. Petersburg (RU); Lubov Borisovna Drozdova, St. Petersburg (RU)

(73) Assignee: Sabic Innovative Plastics IP B.V. (NL)

( * ) Notice: Subject to any disclaimer, the term of this patent is extended or adjusted under 35 U.S.C. 154(b) by 13 days.

(21) Appl. No.: 13/231,276

(22) Filed: Sep. 13, 2011

(65) Prior Publication Data
US 2013/0061657 A1 Mar. 14, 2013

(51) Int. Cl.
| | | |
|---|---|---|
| *G01N 21/00* | (2006.01) | |
| *G01N 33/00* | (2006.01) | |
| *B65D 1/24* | (2006.01) | |
| *B65D 1/36* | (2006.01) | |
| *B65D 25/04* | (2006.01) | |
| *B65D 57/00* | (2006.01) | |
| *C02F 3/02* | (2006.01) | |

(52) U.S. Cl.
USPC .......... 422/82.05; 422/93; 220/553; 220/555; 210/622

(58) Field of Classification Search
None
See application file for complete search history.

(56) References Cited

U.S. PATENT DOCUMENTS

| | | | |
|---|---|---|---|
| 2,619,280 A * | 11/1952 | Redlich | 494/22 |
| 3,231,091 A | 1/1966 | Kingsbury et al. | |
| 3,560,099 A | 2/1971 | Boe et al. | |
| 4,812,294 A * | 3/1989 | Combs | 422/72 |
| 4,892,383 A * | 1/1990 | Klainer et al. | 385/12 |
| 5,007,732 A * | 4/1991 | Ohki et al. | 356/73 |
| 5,162,236 A | 11/1992 | Pang et al. | |
| 5,296,195 A | 3/1994 | Pang et al. | |
| 5,452,232 A | 9/1995 | Espinosa et al. | |
| 5,455,177 A | 10/1995 | Krause et al. | |

(Continued)

FOREIGN PATENT DOCUMENTS

| | | |
|---|---|---|
| JP | 2006242693 A | 9/2006 |
| RU | 2095787 C1 | 11/1997 |

(Continued)

OTHER PUBLICATIONS

Russian Patent No. 2095787 (C1); Publication Date: Nov. 10, 1997; Machine Translation; 7 Pages.

(Continued)

*Primary Examiner* — Jill Warden
*Assistant Examiner* — Brittany Fisher
(74) *Attorney, Agent, or Firm* — Cantor Colburn LLP (57) ABSTRACT

An apparatus and method for spectral analysis of immiscible phases are disclosed. A flow cell for online absorption measurements of immiscible process phases can comprise: a body containing an inlet window and an outlet window in operable communication with a measurement instrument; and a series of partitions that divide the inside of the flow cell into three (3) or more vessels that have an inlet and an outlet, wherein the vessels are connected in series with one another. Optionally, the first vessel is equipped with a porous membrane to facilitate the separation of immiscible process phases.

15 Claims, 4 Drawing Sheets

(56) References Cited

U.S. PATENT DOCUMENTS

| | | | |
|---|---|---|---|
| 5,601,711 A * | 2/1997 | Sklar et al. | 210/238 |
| 5,741,412 A | 4/1998 | Dovichi et al. | |
| 5,770,069 A * | 6/1998 | Meryman | 210/255 |
| 6,297,505 B1 | 10/2001 | Frandsen et al. | |
| 7,247,496 B2 * | 7/2007 | Hochrainer et al. | 436/174 |
| 2004/0197905 A1 * | 10/2004 | Hafeman | 435/374 |
| 2004/0259237 A1 * | 12/2004 | Kellogg et al. | 435/287.1 |
| 2010/0012586 A1 * | 1/2010 | Angelescu et al. | 210/637 |

FOREIGN PATENT DOCUMENTS

| | | |
|---|---|---|
| RU | 2173452 C1 | 12/2000 |
| RU | 2263303 C1 | 6/2004 |
| RU | 63066 U1 | 1/2007 |
| RU | 80240 U1 | 6/2008 |
| RU | 96974 U1 | 8/2010 |
| WO | 2005054182 A1 | 6/2005 |

OTHER PUBLICATIONS

Russian Patent No. 2173452 (C1); Publication Date: Sep. 10, 2001; Machine Translation; 14 Pages.

Russian Patent No. 2263303 (C1); Publication Date: Oct. 27, 2005; Machine Translation; 27 Pages.

Russian Patent No. 63066 (U1); Publication Date: May 10, 2007; Machine Translation; 9 Pages.

Russian Patent No. 80240 (U1); Publication Date: Jan. 27, 2009; Machine Translation; 6 Pages.

Russian Patent No. 96974 (U1); Publication Date: Aug. 20, 2010; Machine Translation; 10 Pages.

Bakeev et al.; "Process Analytical Technology"; Blackwell Publishing; 2005; Chapter 3.4: The Sampling Interface; 17 Pages.

Japanese Patent No. 2006242693 (A); Publication Date: Sep. 14, 2006; Abstract Only; 2 Pages.

International Search Report; International Application No. PCT/US2012/054426; International Filing Date: Sep. 10, 2012; Date of Mailing: Nov. 23, 2012; 5 Pages.

Written Opinion of the International Searching Authority; International Application No. PCT/US2012/054426; International Filing Date: Sep. 10, 2012; Date of Mailing: Nov. 23, 2012; 8 Pages.

* cited by examiner

FLOW CELL FOR MEASURING ELECTROMAGNETIC RADIATION ABSORPTION SPECTRA IN A CONTINUOUSLY FLOWING IMMISCIBLE LIQUID(S) OR LIQUIDS WITH ENTRAINED GAS PHASES

TECHNICAL FIELD

The present invention relates to the area of online measuring equipment and can be used for direct analysis of industrial process streams by absorption spectroscopy analysis.

BACKGROUND

On-line process analysis of industrial streams with flow-through cells containing optical sensors are known. Generally, for industrial process measurements, the sample stream is returned to the process line after the measurement in the flow cell containing an optical sensor so as to avoid product waste. Pretreatment of the process sample is often required prior to measurement.

Generally, a flow cell has two optical windows situated to permit electromagnetic radiation to pass through the first window, through the industrial process stream, and out through the second window. Fiber optic cables are commonly used to guide the input source radiation to the flow cell and also to guide the resulting partially "absorbed" light back to a remotely located spectrometer for measurement.

Simple flow cells constructed of two parallel optical plates are known. The distance between the optical plates is defined as the optical path length. The process liquid flow is analyzed as it passes through the space between the optical windows. Such flow cells have been used for on-line analysis of biological liquids, colloidal dispersed systems, and hydrocarbons. These flow cells are characterized by simple construction and can only be used for sample analyses that do not require sample preparation or pretreatment. Some analyses require careful temperature control, in these cases the flow cell may be placed in a thermostatically controlled bath. This may be particularly useful for reactions where the liberation of heat in the flow cell requires careful temperature control. These measuring cells are limited by the strength of their construction and are not appropriate for measurements at either high pressures or high mechanical stresses.

Flow measuring cells are often used in high performance liquid chromatography (HPLC) analysis and capillary electrophoresis. Flow cells of this type are typically constructed of strong/durable materials, have small volumes, and generally have a short sample "path length". Additional requirements are imposed for industrial process applications due to the elevated mechanical stresses caused by high pressures and high process flow rates. These cells must also be designed to resist the potentially damaging effects of the process medium, e.g., the inlet and outlet channels can be arranged at an angle to the light path direction to reduce mechanical stress on optical windows. The cell-holder may be made of an inert plastic to increase the cell life time when used with corrosive process streams.

Some flow cells are utilized for optical measurements at high process pressures. Other flow cells are designed for light absorption measurements of small liquid volumes. Nickel capillary tubes with polished interior surfaces have been utilized for optical measurements using multiple radiation reflection.

Flow cells with multiple capillary analyzers have been designed for biochemical capillary analysis. The use of flow cells of this type allows minimization of the sample volume. Short path length flow cells may be used for measurements obtained in the ultraviolet, visible or middle infrared region of electromagnetic radiation spectrum. However, the relative absorbance values observed in near infrared region of electromagnetic radiation spectrum are significantly less, thus requiring longer path lengths to minimize sample analysis errors.

Liquids may also contain dissolved gases at high pressure that can interfere with spectroscopic measurements. The arrangement for analytical control of metallurgical production can include an air-separating vessel installed before the measuring cell.

As described above, optical measurements have been carried out for a variety of different process conditions. However, the prior art does not describe a suitable cell design for use in the measurement of process streams containing one or more immiscible liquid phases, or for process streams containing dissolved or bulk gases. The previously described cells may be used for the analysis of homogeneous samples but are inadequate for measurements of process samples having immiscible phases. Process samples containing one or more immiscible phases result in significant light dispersion at the interface of the various phases and result in unacceptable measuring errors.

What is needed in the art is a flow cell capable of measurement of immiscible liquid phases.

SUMMARY

The present disclosure provides for a flow cell for an online absorption measurement of immiscible process phases and methods for using the same.

In one embodiment, a flow cell for an online absorption measurement of immiscible process phases containing liquid phases and/or gas phases, can comprise: a body containing an inlet window and an outlet window in operable communication with a measurement instrument; and a series of partitions that divide the inside of the flow cell into three (3) or more vessels that have an inlet and an outlet, wherein the vessels are connected in series with one another. Optionally, the first vessel is equipped with a porous membrane to facilitate the separation of immiscible process phases.

In one embodiment, a method of making on-line absorption measurements of immiscible phases containing liquid phases and/or gas phases comprises: associating a flow cell with a process stream comprising the immiscible phases; and making a measurement of the immiscible phases. The flow cell can comprise a body containing an inlet window and an outlet window in operable communication with a measurement instrument; and a series of partitions that divide the inside of the flow cell into three or more vessels that have an inlet and an outlet, wherein the vessels are connected in series with one another, and wherein the first vessel is equipped with a porous membrane.

In another embodiment, a method of making on-line absorption measurements of immiscible fluid phases, comprises: introducing the immiscible fluid to a flow cell; separating the immiscible fluid phases within the flow cell using a porous membrane and partitions; and making a measurement of said separated immiscible fluid phases.

These and other non-limiting characteristics are more particularly described below.

BRIEF DESCRIPTION OF THE DRAWINGS

Refer to the drawings, which are exemplary, not limiting, and wherein like elements are numbered alike.

DETAILED DESCRIPTION

In order to solve this problem an improved flow cell has been designed and constructed that first separates the various immiscible phases and then allows independent analysis (e.g., spectrophotometric analysis and so forth) of each of the separated phases. In this improved flow cell, a series of communicating vessels was constructed such that the separation of the immiscible phases occurs in the first vessel and the separated phases are subsequently directed to different vessels. Electromagnetic radiation absorption spectra for each of the various phases may then be obtained for each of the phases independently resulting in improved detection limits and accuracy. Measurements may be carried out on one or all of the separated phases as required by the particular process application.

Definitions

The singular of a word can mean the plural, unless specifically directed otherwise.

"Combination" is inclusive of blends, mixtures, alloys, reaction products, and the like.

The terms "first," "second," and the like, herein do not denote any order, quantity, or importance, but rather are used to d one element from another.

The terms "a" and "an" and "the" herein do not denote a limitation of quantity, and are to be construed to cover both the singular and the plural, unless otherwise indicated herein or clearly contradicted by context.

The suffix "(s)" as used herein is intended to include both the singular and the plural of the term that it modifies, thereby including one or more of that term (e.g., the cell(s) includes one or more cells).

Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

"Light" and "heavy" liquid are relative terms to identify that the density of one liquid is less than the density of another liquid, respectively. One of ordinary skill in the art can understand the meaning of these terms in the context of this disclosure.

A "partition" can include a baffle.

"Fast Loop" means a channel or a pipe passing a part of stream to be analyzed around the cell to reduce the stream rate to an optimal value. The Fast Loop 400, i.e., bypass, allows sufficient sample flow to insure that the sample being measured is close in time to the process, thereby preventing significant delays in analysis.

As stated above, the disclosure is directed to a flow cell containing apparatus for on-line monitoring and a method for making spectral measurements of immiscible liquids and/or gas phases utilizing electromagnetic radiation, which utilize said apparatus.

The flow cell, which is described in more detail below, is cable of withstanding the process stream conditions to which it is subjected. The flow cell serves as a medium to which collection of information can occur for fluids (liquids and/or gases). The flow cell has sensors (e.g., spectral sensors) in communication with the flow cell so that measurements (e.g., spectral measurements) can be collected. Plumbing, which for purposes of this disclosure includes electrical connections and necessary conduits that place various constituents of the apparatus in communication with the flow cell, e.g. optical sensors and process stream components, can be achieved by one of ordinary skill the art without undue experimentation.

A. Apparatus

In one embodiment, the apparatus includes: a body (e.g., frame, housing, container, etc.) containing inlet window(s) and outlet window(s), wherein, depending upon the measurement instrument requirements, the windows can be optical windows), coupled to (e.g., in operable communication with) measurement instrument(s) (e.g., Raman spectroscopy, fluorescence spectroscopy, refractive index measurements, gas chromatography, liquid phase chromatography, mass spectrometry, as well as combinations comprising at least one of the foregoing), a series of partitions, e.g. baffles, that divide the inside of the flow cell into three (3) or more vessels that have inlet(s) and outlet(s).

The flow cell embodied by this disclosure is associated with a process stream, e.g. an industrial process stream. One of ordinary skill in the art would be able to configure the plumbing for associating the flow cell with a process stream. This can be done without undue experimentation.

The materials for construction of the flow cell are chosen such that the, gaskets, fittings, and body of the cell are stable to all compositions of the phases to be analyzed, and, if a spectroscopic measurement will be taken, sufficiently rigid such that the optical path length of the cell does not vary when exposed to the process measurement conditions. Desirably, the optical windows are situated at about 85 to 105 degrees (desirably 90 degrees) to the process flow and both the source (optical entry to the cell) and the exit (optical path leaving the cell) can be aligned to minimize optical losses.

Optical windows can be formed from any material that is transparent to the wavelengths used for a particular process analysis, e.g., a transmission that is sufficient to allow for quality measurements at desired signal to noise ratio. In various embodiments, the material can have a transmission of greater than or equal to 80%, specifically, greater than or equal to 90%, and more specifically, greater than or equal to 95%, as measured according to ASTM D1003-07, Procedure A, measured, e.g., using a HAZE-GUARD DUAL from BYK-Gardner, using and integrating sphere (0°/diffuse geometry), wherein the spectral sensitivity conforms to the International Commission on Illumination (CIE) standard spectral value under standard lamp D65.

Some examples of possible materials include synthetic sapphire, quartz, glass (e.g., borosilicate glass), plastics (e.g., optical grades of polycarbonate, acrylics, and so forth), etc. that have the desired transmissivity and are compatible with the process stream.

The physical parameters, include, but are not limited to, a partition height that can be moderated by one of ordinary skill in the art to achieve a desired ratio of heights so as to achieve the necessary separation of liquid(s) and/or gas(es). This can be done without undue experimentation.

The porous membrane can be a coalescing film. The coalescing film (porous material) should be able to separate the various non-continuous phases by coalescing the dispersed particles or droplets, desirably in a reasonable time. In general, a porous material which has a strongly different wetting angle for the phases to be separated is desirable. Proper porosity of the coalescing media is also a factor. If the pores are too large, not all of the dispersed drops will contact the coalescing media. Any droplets that are not coalesced into the proper phase will result in higher measurement errors. The presence of surfactants can make this difficult or impossible. Some materials used for constructing coalescing films include fluorinated materials, silicon materials, or combined silicon/fluorinated materials. These materials are poorly wetted by the aqueous phase, and as such function to reject water while passing predominantly organic and gas phases.

Spectral measurements can be made by a variety of techniques that are compatible with measurement in a liquid and/or gas stream. Methods of spectral measurement include, but are not limited to, ultraviolet, visible, and/or infrared electromagnetic radiation.

In one embodiment, the spectroscopic instruments utilize fiber optic cables.

The flow cell, which is a receptacle for an industrial process medium, e.g. fluid medium (i.e., liquid and/or gas medium), must be capable of measurement by spectral analysis.

In one embodiment, the cell is designed for measurement utilizing ultraviolet, visible and/or infrared electromagnetic radiation. Spectral measurement apparatuses can be connected to the flow cell without undue experimentation.

The orientation of the vessels in the apparatus depends on what is being measured in the system.

In one embodiment, the flow cell has at least two communicating vessels for measurements of the separated light phase.

In another embodiment, there are at least four communicating vessels for measurements carried out in two liquid phases and/or a gas phases.

Figure 1:
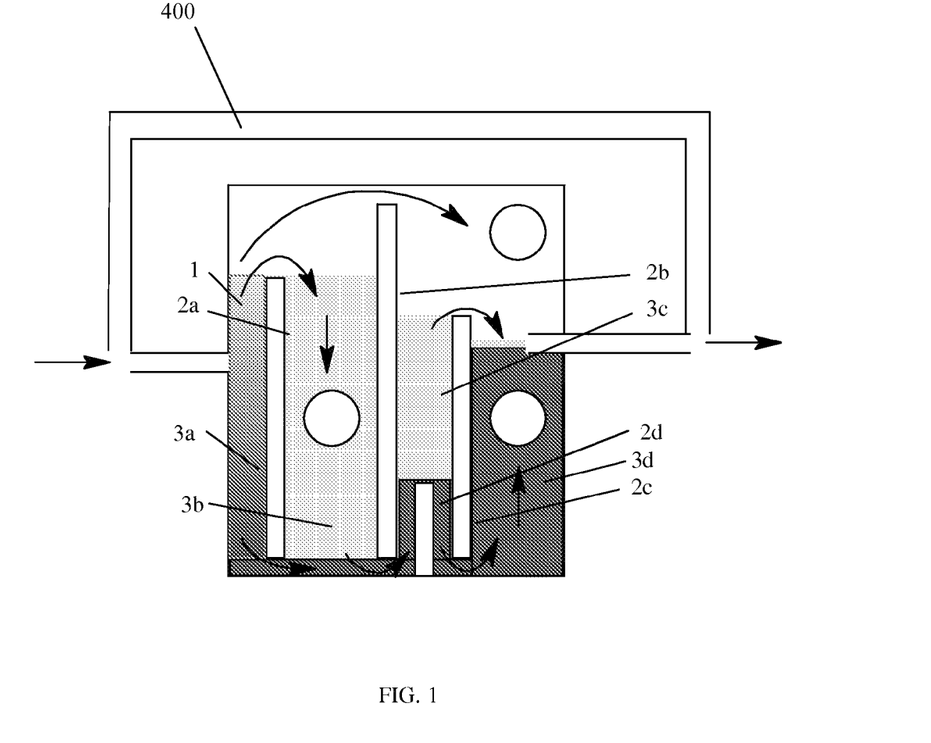
FIG. 1 shows a schematic of a flow cell according to one embodiment of the claimed invention.

A schematic of the improved flow cell is presented in FIG. 1. This flow cell is designed for electromagnetic radiation absorption measurements in industrial streams containing of one or more immiscible phases where one of the immiscible phases may be a gas phase.

The flow cell can comprise of a body 1 and built-in partition(s) 2a, 2b, and 2c, and optionally 2d. Partitions divide the cell into vessels 3a, 3b, 3c, 3d. The height of partition 2b is greater than the height of partition 2a; the height of partition 2c is less than the height of partition 2a. The ratio of partition heights of each respective partition depends on the ratio of densities of the phases. The 2b/2c height ratio must exceed heavy liquid/light liquid density ratio, and 2a height is approximately the average of 2b and 2c heights. At the same time the 2a height/outlet height must be less than the heavy liquid/light liquid density ratio.

A process stream consisting of at least of two immiscible phases enters vessel 3a where a separation occurs. The separation of the immiscible phases is facilitated by the placement of a porous membrane in vessel 3a. The membrane is chosen with surface properties such that it improves the separation of the two phases entering the cell.

The heavy phase then passes into vessel 3b through the lower channel while the lighter phase passes into vessel 3b through the upper channel. From the lower part of the vessel 3b two phases go into vessel 3c. Absorbance measurements are carried out in vessel 3b. In the described cell design only the light phase is in the upper channel and there is only the heavy phase below the lower channel. By first separating the immiscible phases, the spectroscopic measurement is not subject to light dispersion at the interfaces and the measurement accuracy is greatly improved. From vessel 3c the heavy phase goes into vessel 3d through the lower channel; and the light phase goes into vessel 3d through upper channel. An auxiliary partition 2d is located in vessel 3b which prevents the light phase from going into vessel 3d through the lower channel. Measurements of the heavy phase absorbance are carried out in the vessel 3d. Only the heavy phase is found below the upper channel.

In the event that a gas phase is present in the process stream, it goes into the output stream through the common gas space of all vessels 3a, 3b, 3c, and 3d. Measurements may also be carried out on the gas phase as required.

At the outlet from vessel 3d all of the separated phases are recombined and may be returned to the original process stream without any changes.

The flow rate through the flow cell is selected such that the various phases have adequate time to phase separate. One of ordinary skill in the art can adjust the flow rate without undue experimentation.

The flow cell proposed has been used for on-line spectrometry compositional measurements of cumene oxidation products. In the "wet" oxidation of cumene, the oxidation product is a mixture of water and organic phases and an additional gas phase. Water, the organic (cumene) layer and the gas phase were separated with the improved cell. Spectroscopic measurements were carried out in the near infrared region of electromagnetic radiation spectrum. Cumene hydroperoxide (CHP) concentration was measured.

Figure 2:
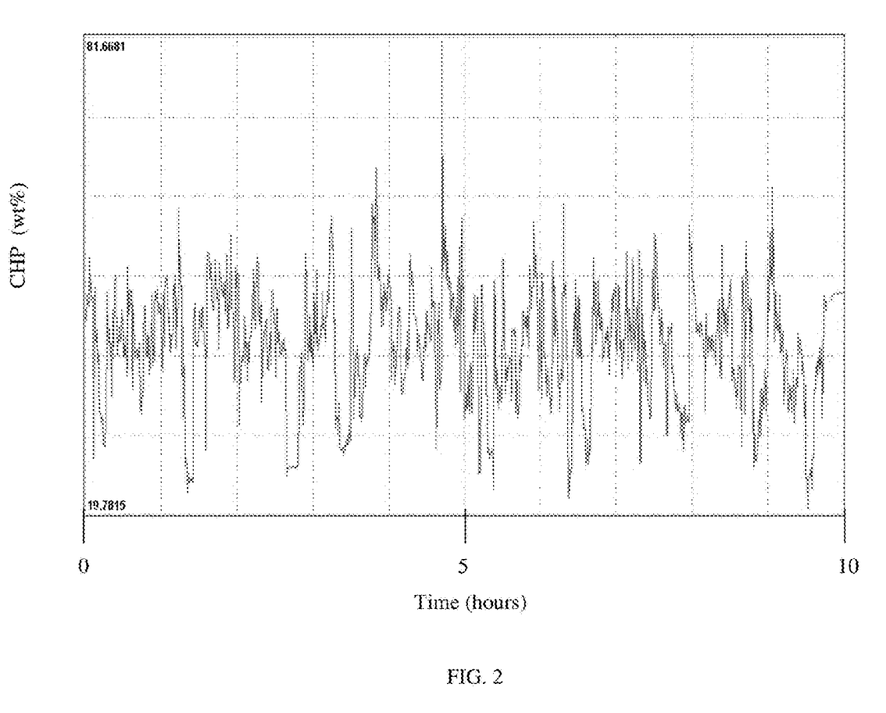
FIG. 2 is a graph of cumene hydroperoxide (CHP) concentration over a period of 10 hours measured using a typical cell. The X-axis is time in hours and Y-axis is CHP weight percent (wt %) (from 19.7815 to 81.6681).

FIG. 2 is a graph of CHP concentration over a period of 10 hours measured using a typical cell. The measurement values are not reproducible and relative measurement error of up to 100% is common.

Figure 3:
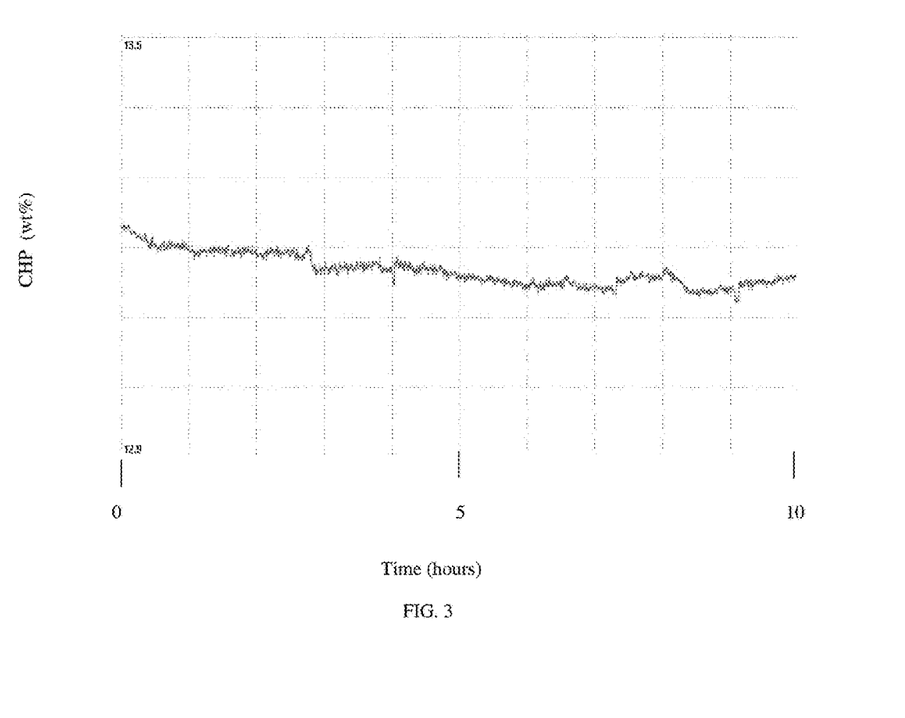
FIG. 3 is a graph of CHP concentration over a period of 10 hours measured using the proposed improved flow cell. The X-axis is time in hours and Y-axis is CHP wt. % (from 12.9 to 13.5).

FIG. 3 is a graph of CHP concentration over a period of 10 hours measured using the proposed improved flow cell. The measurement error did not exceed 0.2%.

Figure 4:
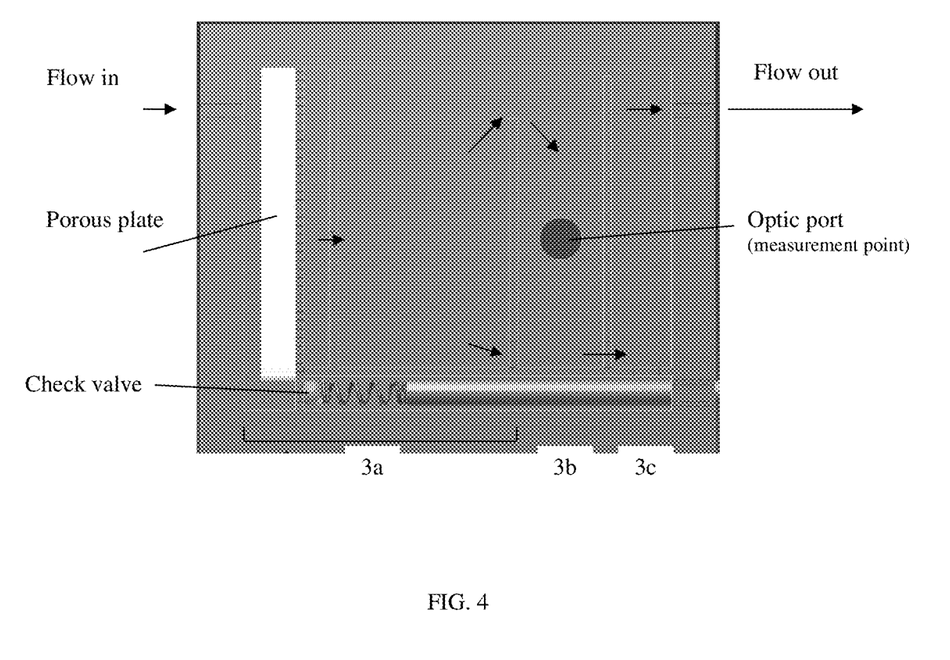
FIG. 4 is a schematic of a flow cell for the measurement of cumene hydroperoxide concentration in a cumene oxidation stream.

FIG. 4 represents the scheme of a flow cell for the measurement of cumene hydroperoxide concentration in a cumene oxidation stream, which contains a water phase and dissolved air with a porous fluoropolymer plate for layers coalescing, and a check valve to provide a pressure drop for pushing the fluid though this plate; vessel 3a in this case is specially designed to hold this. A part of a full flow passes through the bottom channel to optimize phase coalescing process.

In another embodiment, various embodiments in the dependent claims can be integrated with one another, as well as into an independent claim.

B. Method of Monitoring

As stated above, the disclosure also provides for a method of making on-line absorption measurements of immiscible fluid phases (e.g., liquid phases and/or gas phases).

Referring to FIG. 1, the head chamber splits (e.g., separates) the mixed phases into two or more separate phases that can then be further separated for analysis. This separation can be facilitated using a coalescer 2a where the incoming flow enters the cell. The size of chamber and of the coalescer depends on a number of factors: (a) the relative densities of the immiscible phases (the greater the phase densities are, the faster they will separate, thus enabling a smaller chamber 2a, and conversely, small differences in phase densities will result in larger coalescers and chambers); (b) the initial size of the dispersed phase particles (droplets) in the input flow (the smaller the particles or droplets, the more time needed for settling, resulting in a larger 2a chamber); and (c) the performance of the coalescing film (porous material) with respect to the particular process stream that is to be analyzed. If the performance is ideal, and separation is readily made the size of the chamber and coalescing film may be minimized. In the event that the coalescing film passes only a single phase, the optical measurements can be made directly. (However, in this case, only one of the phases is generally free of the other phases.) Another factor is the amount of gas phase present in the input flow. Large gas flows are able to disturb the liquid surface inside the flow cell resulting in less stable operation. In these cases more open surface area is used for chamber 2a. Taking these various factors into consideration when designing the cell, the incoming mixed phases can be separated or "split" into continuous immiscible phases. These can be further separated in the tailing chambers prior to analysis (e.g., spectrophotometric measurement).

The tail chambers 2b, 2c, 2d function to direct the various (now continuous) phases to a separate chamber for analysis (e.g., optical analysis), wherein each chamber can be filled as a function of its phase density. The light liquid phase (lowest density) passes to chamber 2b. The heavy phase passes to chamber 2d. Chamber 2c provides a bypass around chamber 2d for the light phase. Measurements can then be taken of the separated phases (e.g., pure separated phases) in the corresponding chamber as required for the particular process stream. In the event that analyses of both light and heavy phases are not desired, chambers 2b and 2c, or chambers 2c and 2d may be combined respectively. This last case is presented in FIG. 4.

The orientation of the vessels in the apparatus depends on what is being measured in the system.

In one embodiment, the cell has at least two communicating vessels for measurements of the separated light phase.

In another embodiment, there are at least four communicating vessels for measurements carried out in two liquid phases and/or a gas phase.

Spectral measurements can be done on a varying basis. In one embodiment, the spectral measurements are made on a continuous basis, intermittent basis, or a preprogrammed or set basis.

Optionally, a feedback loop to an industrial process, can be designed and implemented with the end goal of automating the industrial process, for example, a controller, (e.g. a program logic controller) can be programmed to effectuate a desired relay signal back to an industrial system device to make a necessary change in an operating condition.

The flow cell provides clean continuous phases for light absorption measurements. The flow cell can also be useful for other optical measurements sensitive to flow turbidity or when the presence of several phases may interfere with the desired measurements. Analyses methods such as, Raman spectroscopy, fluorescence spectroscopy, and refractive index measurements may benefit from sample phase separation prior to analysis. In addition, this cell may also be used as a "sample preparation" step for other types of online analysis such as gas chromatography, liquid phase chromatography, mass spectrometry, etc. In these cases the design of the cell is similar; the optical windows would be optional. (Although, they may still be useful for setting up or monitoring the function of the cell as a separator.)

In an embodiment, various embodiments in the dependent claims can be integrated with one another, as well as into an independent claim.

In one embodiment, a flow cell for online absorption measurements of immiscible fluids (e.g., liquids and/or gas phases) utilizing electromagnetic radiation, comprises: a housing containing one or more inlet optical windows and one or more outlet optical windows in communication with one or more remote spectroscopic instruments, a series of partitions that divide the inside of the flow cell into three (3) or more vessels that have one or more inlets and one or more outlets that are connected in series with one another, wherein the first vessel is equipped with a porous membrane to facilitate the separation of immiscible process phases.

In another embodiment, a flow cell for online absorption measurements of immiscible process phases containing liquid phases and/or gas phases, can comprise: a body containing an inlet window and an outlet window in operable communication with a measurement instrument; and a series of partitions that divide the inside of the flow cell into three (3) or more vessels that have an inlet and an outlet, wherein the vessels are connected in series with one another. The first vessel can be equipped with a porous membrane to facilitate the separation of immiscible process phases.

In one embodiment, a method of making online absorption measurements of immiscible fluid (liquids and/or gas) phases utilizing electromagnetic radiation for a process stream analysis, can comprise: providing a flow cell containing a housing containing one or more inlet optical windows and one or more outlet optical windows in communication with one or more remote spectroscopic instruments, a series of partitions that divide the inside of the flow cell into three (3) or more vessels that have one or more inlets and outlets that are connected in series with on another, wherein the first vessel is equipped with a porous membrane to facilitate the separation of immiscible process phases; associating the flow cell with a process stream; and making a spectral measurement(s) of said immiscible process phases.

In another embodiment, a method of making on-line absorption measurements of immiscible fluid (liquids and/or gas) phases, can comprise: introducing the immiscible fluid to a flow cell; separating the immiscible fluid phases within the flow cell using a porous membrane and partitions; and making a measurement of said separated immiscible fluid phases.

In the various embodiments, (i) the porous membrane can be a fluorinated material and/or silicon material; and/or (ii) there can be at least two communicating vessels for measurements of the separated light phase; and/or (iii) there can be at least four communicating vessels for measurements, e.g., carried out in two liquid phases and/or a gas phase; (iv) the flow cell can be designed for measurements utilizing ultraviolet, visible, and/or infrared electromagnetic radiation; and/or (v) the flow cell can include a Fast Loop by pass line; and/or (vi) one or more remote spectroscopic instruments can utilize fiber optic cables; and/or (vii) spectral measurements can be made on a continuous basis; and/or (viii) the spectral measurements can be made on an intermittent basis; and/or (ix) the spectral measurements can be made on a pre-programmed or set basis; and/or (x) the membrane can be located in a first vessel of the flow cell; and/or (xi) the measurement is selected from the group consisting of spectroscopy, refractive index measurements, chromatography, chromatography, spectrometry, and a combination comprising at least one of the foregoing; and/or (xii) the measurement instrument can be selected from the group consisting of Raman spectroscopy, fluorescence spectroscopy, refractive index measurements, gas chromatography, liquid phase chromatography, mass spectrometry, and a combination comprising at least one of the foregoing.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A flow cell for online absorption measurements of immiscible process phases containing liquid phases and/or gas phases, comprising:
    a body containing an inlet and an outlet associated with a process stream, and an inlet window and an outlet window in operable communication with a measurement instrument; and
    a series of partitions that divide the inside of the flow cell into three (3) or more vessels that have an inlet and an outlet, wherein the vessels are connected in series with one another, and wherein the first vessel is equipped with a porous membrane to facilitate the separation of immiscible process phases; and
    wherein the process phases are recombined prior to the outlet of the body.

2. The flow cell according to claim 1, wherein the membrane is located in the first vessel of the flow cell, and wherein the porous membrane is a fluorinated material and/or silicon material.

3. The flow cell according to claim 1, wherein there are at least two communicating vessels for measurements of a separated light phase.

4. The flow cell according to claim 1, wherein there are at least four communicating vessels for measurements carried out in two liquid phases and/or a gas phase.

5. The flow cell according to claim 1, wherein the flow cell is designed for measurements utilizing ultraviolet, visible, and/or infrared electromagnetic radiation.

6. The flow cell according to claim 1, further comprising a Fast Loop by pass line.

7. The flow cell according to claim 1, wherein the measurement instrument is selected from the group consisting of Raman spectroscopy, fluorescence spectroscopy, refractive index measurements, gas chromatography, liquid phase chromatography, mass spectrometry, and a combination comprising at least one of the foregoing.

8. The flow cell according to claim 7, wherein the measurement instrument comprises a remote spectroscopic instrument.

9. The flow cell according to claim 8, wherein the remote spectroscopic instrument utilizes fiber optic cable.

10. A method of making on-line absorption measurements of immiscible phases containing liquid phases and/or gas phases comprising:
    configuring a flow cell to receive a process stream comprising the immiscible phases; and
    making a measurement of the immiscible phases;
    wherein the flow cell comprises a body containing an inlet and an outlet associated with the process stream, and an inlet window and an outlet window in operable communication with a measurement instrument; and a series of partitions that divide the inside of the flow cell into three or more vessels that have an inlet and an outlet, wherein the vessels are connected in series with one another, and wherein the first vessel is equipped with a porous membrane to facilitate the separation of immiscible process phases; and
    wherein the process phases are recombined prior to the outlet of the body.

11. The method of claim 10, wherein the measurement is made on a continuous basis, intermittent basis, or a preprogrammed or set basis.

12. The method of claim 10, wherein the measurement is selected from the group consisting of spectroscopy, refractive index measurements, chromatography, chromatography, spectrometry, and a combination comprising at least one of the foregoing.

13. The flow cell according to claim 1, wherein the inlet window is located between the first and second partitions.

14. The flow cell according to claim 1, wherein the inlet and outlet windows are situated at about 85 to about 105 degrees to the process flow.

15. The flow cell according to claim 1, wherein the height of the first partition is less than the height of the second partition and greater than the height of the third partition.

* * * * *